United States Patent [19]
Scherberich

[11] 3,980,666
[45] Sept. 14, 1976

[54] PROCESS FOR THE RESOLUTION OF D,L-PENICILLAMINE AND SALTS FORMED DURING SAID PROCESS

[75] Inventor: Paul Scherberich, Dietzenbach, Germany

[73] Assignee: Deutsche Gold- und Silber-Scheideanstalt vormals Roessler, Frankfurt, Germany

[22] Filed: Dec. 16, 1974

[21] Appl. No.: 532,936

[30] Foreign Application Priority Data
Dec. 17, 1973  Germany............................ 2362687

[52] U.S. Cl........................ 260/306.7 C; 260/534 S
[51] Int. Cl.²......................................... C07D 277/06
[58] Field of Search.................. 260/306.7 C, 534 S

*Primary Examiner*—Richard J. Gallagher
*Attorney, Agent, or Firm*—Cushman, Darby & Cushman

[57] ABSTRACT

D,L-penicillamine is separated into its antipodes employing optically active threo-1-(p-nitrophenyl)-2-aminopropanediol-1,3.

24 Claims, No Drawings

PROCESS FOR THE RESOLUTION OF D,L-PENICILLAMINE AND SALTS FORMED DURING SAID PROCESS

The invention is directed to a process for the recovery of optical isomers of penicillamine by resolving D,L-penicillamine by means of optically active bases.

It is known that the resolution of a racemic modification into the two antipodes is a difficult matter and the finding of a satisfactory resolving agent is a matter of trial and error, see Eliel "Stereochemistry of Carbon Compounds" pages 49–50 (1962).

The optical isomers of the aminoacid penicillamine have valuable therapeutic properties. For example D-penicillamine is an important medicine for treating Morbus Wilson, defect schizophrenia, sclerodermia, cystinuria, chronic aggressive hepatitis especially in the basic therapy or rheumatoid arthrites. It also is used as an antidote in heavy metal poisoning.

It is known to recover the optically active isomers D-penicillamine or L-penicillamine by resolving D,L-penicillamine by means of optically active bases. As optically active bases there have been used d-pseudo-ephedrine, l-ephedrine or l-norephedrine or alkaloids such as brucine, thebaine, quinidine or cinchonidine. In carrying out the resolution first protective groups are introduced into the penicillamine molecule so that derivatives of penicillamine are present for the resolution. Suitable derivatives for example are the N-acyl products of D,L-penicillamine or S-benzyl-D,L-penicillamine, as well as the acylation products of the reaction product of D,L-penicillamine with carbonyl compounds. (The Chemistry of Penicilline, Princeton University Press, 1949); Wellcome British Pat. No. 585,413, Duffin U.S. Pat. No. 2,450,784, duVigneaud U.S. Pat. No. 2,543,358, Mozingo U.S. Pat. No. 2,539,854 and German Offenlegungschrift No. 2,138,122 and Asinger U.S. application Ser. No. 419,473 filed Nov. 27, 1973. Asinger is a continuation-in-part of abandoned application Ser. No. 276,530 filed July 31, 1972. The entire disclosure of the Asinger U.S. application and the United States and British patents, German Offenlegungsschrift and The Chemistry of Penicilline are hereby incorporated by reference and relied upon.

There has now been found a process for the recovery of the optical isomers of penicillamine by means of an optically active base characterized by the fact that there is used as the optically active base an optically active form of threo-1-(p-nitrophenyl)-2-amino-propanediol-1,3

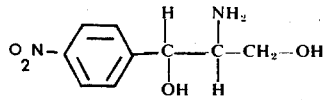

I

The D-penicillamine is recovered using D-(−)-threo-1-(p-nitrophenyl)-2-amino-propanediol-1,3 and the L-penicillamine is recovered using L-(+)-threo-1-(p-nitrophenyl)-2-amino-propanediol-1,3.

The process of the invention is considerably less expensive than the known processes. The diastereomeric salts formed are distinguished by especially large differences in solubilities and in this differ advantageously from the diastereomeric salts which occur with the previously used optically active bases. Both the D-penicillamine and the L-penicillamine precipitate in excellent yields and in high purity. The threo-1-(p-nitrophenyl)-2-amino-propanediol-1,3 or its optically active isomers are more easily accessible than the optically active bases for the known processes; the threo-1-(p-nitrophenyl)-2-amino-propanediol-1,3 after its use for the racemic splitting can be recovered almost completely in an especially simple manner and in pure form.

The threo-1-(p-nitrophenyl)-2-amino-propanediol-1,3 used in the invention can be produced in known manner, for example according to the process of Ehrhart German Pat. No. 839,500 or split into its optical isomers with optically active tartaric acid according to the process of Lepetit British Pat. No. 674,015.

The optical isomers of threo-1-(p-nitrophenyl)-2-amino-propanediol-1,3 can be added either as the free bases or in the form of their salts. As salts there can be used both salts with inorganic acids, e.g., mineral acids and organic acids. As mineral acid salts, there can be used for example the sulfate, hydrogen sulfate, phosphate, hydrogen phosphate, nitrate or preferably the hydrohalides, especially the hydrochloride.

As salts with organic acids there can be used salts such as those with sulfonic acids or preferably with carboxylic acids. As sulfonic acids there can be used for example aliphatic sulfonic acids, e.g., alkane sulfonic acids such as methane sulfonic acid, methane trisulfonic acid, propane-2-sulfonic acid, butane-1-sulfonic acid, or aromatic sulfonic acids such as p-toluene sulfonic acid or naphthalene sulfonic acid or especially benzene sulfonic acid. As carboxylic acids there can be used for example saturated or unsaturated mono and polycarboxylic acids, in a given case substituted by —OH, —NH$_2$, —NHR,

—OR, —SH, —SR, or halogen, e.g., F, Cl or Br and where R, R$_3$ and R$_4$ are alkyl or aryl, e.g., methyl, ethyl, propyl, butyl, amyl, decyl, phenyl or tolyl. Examples of such acids include isobutyric acid, valeric acid, isovaleric acid, trimethylacetic acid, lactic acid, oxalic acid, malonic acid, adipic acid, maleic acid, succinic acid, glutaric acid, azelaic acid, sebacic acid, tartaric acid, citric acid, espcially acids containing 1 to 6 carbon atoms, e.g., alkanoic acids such as formic acid, acetic acid and propionic acid or araliphatic acids such a phenylacetic acid, mandelic acid, aromatic acids, especially 3-phenylpropionic acid or aromatic carboxylic acids such as phthalic acid, terephthalic acid, isophthalic acid, salicyclic acid and especially benzoic acid, or heteroaromatic carboxylic acids such as thiophene-2-carboxylic acid, thiazole-4-carboxylic acid, furane-2-carboxylic acid, picolinic acid and isonicotinic acid.

In using the mineral acid salts it is suitable to add equivalent amounts of organic or inorganic alkaline acting substances. As such there are preferably used tertiary amines such as triethylamine or pyridine or alkali hydroxyides such as potassium hydroxide or sodium hydroxide.

As in the known processes for resolution the D,L-penicillamine in the process of the invention first must be converted into a suitable derivative for the resolution before the reaction with the optically active base can take place. Preferably the protection is provided by converting the D,L-penicillamine into a thiazolidine-4-carboxylic acid of the formula:

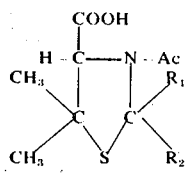

In the formula, $R_1$ and $R_2$ can be the same of different and are hydrogen, alkyl of 1 to 8 carbon atoms or $R_1$ and $R_2$ can be joined with the adjacent carbon atom to form a hydrocarbon ring with 4 to 10 carbon atoms. Ac is an acyl group, especially benzoyl, tosyl, nitrophenylsulfenyl, lower alkanoyl, e.g., acetyl or preferably formyl.

Of these protected compounds there are preferred those in which the D,L penicillamine is converted into an N-acetyl or, preferably N-formyl derivative of a 2,2-dialkyl-5,5-dimethyl thiazolidine-4-carboxylic acid. Of these there is preferred N-formyl-2,2,5,5-tetramethylthiazolidine-4-carboxylic acid (N-formyl-isopropylidene-D,L-penicillamine) and D,L-3-formyl-2,2-pentamethylene-5,5-dimethyl-thiazolidine-4-carboxylic acid. These thiazolidine-4-carboxylic acids can be made in a simple manner from D,L-penicillamine and the corresponding carbonyl compounds (The Chemistry of Penicilline (1949), Princeton University Press).

Other thiazolidine-4-carboxylic acids which can be used and which are within formula II include D,L-3-acetyl-2,2,5,52,2,5,5-tetramethyl-thiazolidine-4-carboxylic acid, D,L-3-propionyl-2,2,5,5-tetramethyl thiazolidine-4-carboxylic acid, D,L-3-benzoyl-2,2,5,5-tetramethyl-thiazolidine-4-carboxylic acid, D,L-3-p-toluenesulfenyl-2,2,5,5-tetramethyl-thiazolidine-4-carboxylic acid, D,L-3-p-nitrophenylsulfenyl-2,2,5,5-tetramethyl-thiazolidine-4-carboxylic acid, D,L-3-formyl-2,2-diethyl-5,5-dimethyl-thiazolidine-4-carboxylic acid, D,L-3-formyl-2,2-dioctyl-5,5-dimethylthiazolidine-4-carboxylic acid, D,L-3-formyl-2,2-tetramethylene-5,5-dimethyl-thiazolidine-4-carboxylic acid, D,L-3-formyl-2,2-dibutyl-5,5-dimethyl-thiazolidine-4-carboxylic acid, D,L-3-formyl-2,2-dicyclohexyl-5,5-dimethyl-thiazolidine-4-carboxylic acid, D,L-3-formyl-2,2-diphenyl-5,5-dimethylthiazolidine-4-carboxylic acid, D,L-3-formyl-2,2-di-o-tolyl-5,5-dimethyl-thiazolidine-4-carboxylic acid, D,L-3-acetyl-2,2-dihexyl-5,5-dimethyl-thiazolidine-4-carboxylic acid.

As solvents for the resolution there can be used water or more preferably organic solvents such as alcohols, halogenated aliphatic hydrocarbon, ethers, ketones, esters, aromatic hydrocarbons, etc. There are preferably used benzene, toluene, isopropanol and lower carboxylic acid esters, e.g., ethyl acetate, n-butyl acetate, or mixtures of such solvents.

Specific examples of additionally suitable solvents include methanol, ethanol, butanol, isoctyl alcohol, isodecyl alcohol, dodecyl alcohol, chloroform, carbon tetrachloride, dichloroethylene, 1,1,2,2-tetrachloroethane, dibromoethylene, acetone, methyl ethyl ketone, methyl butyl ketone, diethyl ketone, diethyl ether, dimethyl ether, dipropyl ether, dibutyl ether, ethyl formate, ethyl propionate, methyl formate, ethyl formate, ethyl propionate, ethyl butyrate, propyl acetate, ethyl propionate or dioxane.

In the carrying out of the process of the invention there is first provided that the D,L-penicillamine is converted in known way to a suitable derivative (protected D,L-penicillamine) and this is dissolved in water or preferably in an organic solvent or mixture of organic solvents such as those set forth above and this solution in a given case with heating mixed with the optically active threo-1-(p-nitrophenyl)-2-aminopropanediol-1,3 or its salts, in a given case dissolved in an organic solvent such as any of those set forth above. Frequently immediately or, under some conditions, only after long standing, in a given case at low temperatures and after inoculation the more difficulty soluble salt of the optically active penicillamine derivative and optically active threo-1-(p-nitrophenyl)-2-aminopropanediol-1,3 precipitates out while the diastereoisomeric salt, the optical antipode or the racemic mixture or mixtures thereof remains in the mother liquor.

By using D-(−)-threo-1-(p-nitrophenyl)-2-aminopropanediol-1,3 as the optically active base there is obtained as the more difficulty soluble salt that with the D-penicillamine derivative. In like manner by the addition of L-(+)-threo-1-(p-nitrophenyl)-2-aminopropanediol-1,3 there is obtained the salt with the L-penicillamine derivative as the more difficulty soluble salt.

However, the process can also be revised and the solution of the optically active threo-1-(p-nitrophenyl)-2-amino-propanediol-1,3 or its salts, by adding the hydrochloride, preferably with addition of equivalent amounts of organic or inorganic alkaline acting substances be mixed with the derivate of the racemic penicillamine, which if desired is dissolved in a solvent such as the organic solvents set forth above for example.

The process of the invention is advantageously carried out using 0.1 to 3 moles, preferably 0.5 to 1.1 moles of optically active threo-1-(p-nitrophenyl)-2-amino-propanediol-1,3 per mole of racemate. In all ranges the more difficulty soluble salt of the optically active penicillamine derivative and optically active base precipitates. Using less than 0.5 mole of the optically active base there remains in the mother liquor the racemate and optical antipode of the penicillamine derivative; using per mole of racemate between 0.5 and < 1 mole of the optically active base the mother liquor still contains besides the optical antipodes diastereomer salt. If there is added per mole of racemate more than 1 mole of the optically active base there is still contained in the mother liquor in addition to the diastereomeric salt some optically active base.

The salt of the penicillamine derivative and threo-1-(p-nitrophenyl)-2-amino-propanediol-1,3 accumulating in the reaction can be recovered in pure form in known manner because of its very favorable solubility relation, for example by filtration, evaporation of the mother liquor and purification by recrystallization.

The splitting of the more difficulty soluble salt likewise occurs in known manner through treatment with preferably aqueous mineral acids, for example dilute hydrochloric acid (or any of the other mineral acids mentioned above), whereby first the optically active base is recovered in the form of the mineral acid salt and the desired optically active penicillamine derivative is obtained.

The splitting of the D-penicillamine derivative likewise takes place in known manner by splitting off the protective group, for example by acid hydrolysis.

In an analogous manner the optically antipode of the penicillamine can be recovered from the mother liquor of the resolution. However, it is also possible to split the salt of the penicillamine derivative and the optically active base present in the mother liquor. For example the splitting can be accomplished by treatment with dilute hydrochloric acid, the optically active penicillamine derivative thus recovered racemerized in known manner and added again into the resolution.

Unless otherwise indicated all parts and percentages are by weight.

In the following example the rotatory power of the substances is also set forth as specific rotation $[\alpha]_D^{20}$ in degrees $\times$ cm$^3$/dm $\times$ g.

EXAMPLE 1

Ninety-three grams (0.5 mole) of D,L-penicillamine hydrochloride in 500 ml of acetone were heated at reflux temperature for 30 minutes under a nitrogen atmosphere. After distilling off the excess acetone there were obtained 113 grams of D,L-2,2,5,5-tetramethyl-thiazolidine-4-carboxylic acid. The yield amounts to 99%.

A mixture of 113 grams (0.5 mole) of D,L-2,2,5,5-tetramethyl-thiazolidine-4-carboxylic acid hydrochloride and 34 grams (0.5 mole) of sodium formate in 600 ml of 99.8% formic acid were mixed with 226 grams of acetic anhydride at 20°C with stirring for 1 hour. After standing for 12 hours at room temperature the mixture was mixed with 200 ml of water and then concentrated to dryness under reduced pressures. The residue was recrystallized from toluene. There were obtained 88 grams, corresponding to 81% yield of D,L-3-formyl-2,2,5,5-tetramethyl-thiazolidine-4-carboxylic acid having a melting point of 139° to 141°C.

Forty-three point five grams (0.2 mole) of D,L-3-formyl-2,2,5,5-tetramethyl-thiazolidine-4-carboxylic acid and 21,2 g (0.1 mole) D-(−)-threo-1-(p-nitrophenyl)-2-amino-propanediol-1,3 were heated in 200 ml isopropanol at reflux for 1 hour. After the reaction mixture was cooled to 20°C the separated salt was filtered under suction. It was washed with 50ml of isopropanol and dried under reduced pressure at 50°C. The yield amounted to 38 grams, corresponding to 89% based on the added racemic penicillamine derivative. The salt had a specific rotation of +28.2° in a 1% solution in ethanol and had a melting point of 188° to 189°C.

The element analysis showed in weight percent

|  | C | H | N | S |
|---|---|---|---|---|
| calculated as $C_{18}H_{27}O_7N_3S$ | 50.33 | 6.34 | 9.80 | 7.50 |
| found | 50.60 | 6.30 | 9.70 | 7.10 |

Twenty-one point five grams (0.05 mole) of the salt of D-3-formyl-2,2,5,5-tetramethyl-thiazolidine-4-carboxylic acid and D-(−)-threo-1-(p-nitrophenyl)-2-aminopropanediol-1,3 were suspended in 100 ml of water. The mixture was treated with stirring at 20° to 25°C with 10 ml of concentrated hydrochloric acid and held a further 30 minutes under stirring at this temperature. Hereby there separated off D-3-formyl-2,2,5,5-tetramethyl-thiazolidine-4-carboxylic acid. This was washed with 20 ml of water and dried under reduced pressure at 50°C. The yield was 9.8 grams, corresponding to 91% based on the added salt. The thiazolidine-4-carboxylic acid had a melting point of 183° to 184°C and had a specific rotation of +53° in a 1% solution in ethanol.

The hydrochloric acid filtrate was made alkaline with concentrated sodium hydroxide solution with cooling, whereupon the D-(−)-threo-1-(p-nitrophenyl)-2-aminopropanediol-1,3 precipitated as a base soluble with difficulty in water. The substance was filtered off with suction, washed with water and dried at 50°C under reduced pressure. The yield amounted to 10 grams, corresponding to 95% based on the added salt. The substance had a melting point of 161° to 163°C and had a specific rotation of −28.5° in 2% hydrochloric acid solution. The product can be used without previous purification for renewed resolution.

Forty-three point five grams (0.2 mole) of the recovered D-3-formyl-2,2,5,5-tetramethyl-thiazolidine-4-carboxylic acid were held at the boiling point under a nitrogen atmosphere for 2 hours in 200 ml of 15% hydrochloric acid. The mixture was then evaporated to dryness under reduced pressure. The residue was dissolved in 200 ml of 96% ethanol. The solution was adjusted to a pH value between 4 and 5 by the addition of triethylamine. Hereby D-penicillamine separated as the base. The substance was filtered off with suction, washed with ethanol and dried under reduced pressure at 50°C. There were obtained 24 grams of D-penicillamine, corresponding to an 80% yield, based on the added D-3-formyl-2,2,5,5-tetramethyl-thiazolidine-4-carboxylic acid. The D-penicillamine had a melting point of 202 to 204°C and had a specific rotation of −62.8° (5 % solution in normal sodium hydroxide solution).

EXAMPLE 2

The procedure employed was the same as in Example 1 except there were reacted 43.5 grams (0.2 mole) of D,L-3-formyl-2,2,5,5-tetramethylthiazolidine-4-carboxylic acid with 21.2 grams (0.1 mole) of L-(+)-threo-1-(p-nitrophenyl)-2-aminopropanediol-1,3 in 200 ml of isopropanol. The salt recovered of L-3-formyl-2,2,5,5-tetramethyl-thiazolidine-4-carboxylic acid and L-(+)-threo-1-(p-nitrophenyl)-2-aminopropanediol-1,3 had a specific rotation of −28.3° (1% solution in ethyl alcohol) and a melting point of 186° to 188°C. The yield amounted to 37 grams, corresponding to 86%.

The splitting of the salt took place according to Example 1. From 21.5 grams (0.05 mole) of the salt there were obtained 9.7 grams, corresponding to 90% yield, of L-3-formyl-2,2,5,5-tetramethyl-thiazolidine-4-carboxylic acid. This had a specific rotation of −54.3° (measured as a 1% solution in ethanol) and a melting point of 182° to 183°C. The further working of L-penicillamine took place as described in Example 1. The recovered L-penicillamine had a specific rotation of +62.8° (5% solution in sodium hydroxide solution), and a melting point of 203° to 204°C. The yield amounted to 78% based on the added L-penicillamine derivative.

EXAMPLE 3

The procedure was the same as in Example 1 but there were employed 43.5 (0.2 mole) of D,L-3-formyl-2,2,5,5-tetramethyl-thiazolidine-4-carboxylic acid and 21.2 grams (0.1 mole) of D-(−)-threo-1-(p-nitrophenyl)-2-amino-propanediol-1,3 in 250 ml of toluene. The recovered salt of D-3-formyl-2,2,5,5-tetramethyl-thiazolidine-4-carboxylic acid and D-(−)-threo-1-(p-nitrophenyl)-2-amino-propanediol-1,3 had a specific rotation of +28.5° (1% solution in ethanol) and a melting point of 187° to 188°C. The yield was 38 grams, corresponding to 89%.

EXAMPLE 4

The procedure was the same as in Example 1 but there were used 43.5 grams (0.2 mole) of D,L-3-formyl-2,2,5,5-tetramethyl-thiazolidine-4-carboxylic acid and 42.5 grams (0.2 mole) of D-(−)-threo-1-(p-nitrophenyl)-2-amino propanediol-1,3 in 300 ml of isopropanol. The recovered salt of D-3-formyl-2,2,5,5-tetramethyl-thiazolidine-4-carboxylic acid and D-(−)-threo-1-(p-nitrophenyl)-2-amino-propanediol-1,3 had a specific rotation of +28.9° (1% solution in ethanol) and a melting point of 187° to 189°C. The yield was 34 grams, corresponding to 79%.

EXAMPLE 5

The procedure of Example 1 was followed but there were used 43.5 grams (0.2 mole) of D,L-3-formyl-2,2,5,5-tetramethyl-thiazolidine-4-carboxylic acid and 25.8 grams -amino-propanediol-0.1 mole) of D-(−)-threo-1-(p-nitrophenyl)-2-aminopropanediol-1,3-formate in 250 ml of toluene. The recovered salt of D-3-formyl-2,2,5,5-tetramethyl-thiazolidine-4-carboxylic acid and D-(−)-threo-1-(p-nitrophenyl)-2-amino-propanediol-1,3 had a specific rotation of +27.8° (1% solution in ethanol) and a melting point of 186° to 188°C. The yield was 33 grams corresponding to 77%.

EXAMPLE 6

The procedure was the same as in Example 1, but there were used 43.5 grams (0.2 mole) of D,L-3-formyl-2,2,5,5-tetramethyl-thiazolidine-4-carboxylic acid and 27.5 grams (0.1 mole) of L-(+)-threo-1-(p-nitrophenyl)-2-amino-propanediol-1,3-acetate in 250 ml of ethanol. The recovered salt of L-3-formyl-2,2,5,5-tetramethyl-thiazolidine-4-carboxylic acid and L-(+)-threo-1-(p-nitrophenyl)-2-amino-propanediol-1,3 had a specific rotation of −28.4° (1% solution in ethanol) and a melting point of 187° to 189°C. The yield was 34.5 grams, corresponding to 80%.

EXAMPLE 7

Twenty-five grams (0.1 mole) of D-(−)-threo-1-(p-nitrophenyl)-2-amino-propanediol-1,3-hydrochloride were suspended in 250 ml of toluene, treated with 9 grams of 45% aqueous sodium hydroxide (0.1 mole) and subsequently heated to complete water removal on the water separater. The mixture was cooled to 50°C and treated with 43.5 grams (0.2 mole) of D,L-3-formyl-2,2,5,5-tetramethyl-thiazolidino-4-carboxylic acid. The further procedure was as in Example 1. The recovered salt of D-3-formyl-2,2,5,5-tetramethyl-thiazolidine-4-carboxylic acid and D-(−)-threo-1-(p-nitrophenyl)-2-amino-propanediol-1,3 was treated with 300 ml of water free warm methanol for the separation of the simultaneously formed sodium chloride. The sodium chloride was filtered off and the filtrate evaporated to dryness. There were recovered 34 grams, corresponding to 79%, of the the salt of D-3-formyl-2,2,5,5-tetramethyl-thiazolidine-4-carboxylic acid and D-(−)-threo-1-(p-nitrophenyl)-2-amino-propanediol-1,3. It had a specific rotation of +29.1° (1% solution in ethanol) and a melting point of 186° to 188°C.

EXAMPLE 8

The procedure was the same as in Example 1, but there were used 43.5 grams (0.2 mole) of D,L-3-formyl-2,2,5,5-tetramethyl-thiazolidine-4-carboxylic acid and 37 grams (0.1 mole) of L-(+)-threo-1-(p-nitrophenyl)-2-amino-propanediol-1,3 benzenesulfonate in 300 ml of toluene. The recovered salt of L-3-formyl-2,2,5,5-tetramethyl-thiazolidine 4-carboxylic acid and L-(+) -threo-1-(p-nitrophenyl)-2-amino-propanediol-1,3 had a specific rotation of −27.8° (1% solution in ethanol) and a melting point of 187° to 189°C. The yield was 32 grams, corresponding to 75%.

EXAMPLE 9

The procedure was the same as in Example 1 but there were employed 51.4 g (0.2 mole) of D,L-3-formyl-2,2-pentamethylene-5,5-dimethyl-thiazolidine-4-carboxylic acid and 21,2 grams (0.1 mole) of D-(−)-threo-1-(p-nitrophenyl)-2-amino-propanediol-1,3 in 250 ml of toluene. The recovered salt of D-3-formyl-2,2-pentamethylene-5,5-dimethyl-thiazolidine-4-carboxylic acid and D-(−)-threo-1-(p-nitrophenyl)-2-amino-propanediol-1,3 had a specific rotation of −23°(1% solution in ethanol) and a melting point of 182° to 184° C. The yield was 40 grams, corresponding to 85 %.

EXAMPLE 10

Twenty-five grams (0.1 mole) of D-(−)-threo-1-(p-nitrophenyl)-2-amino-propanediol-1,3-hydrochloride were suspended in 250 ml of toluene, treated with 9 grams of 45 % aqueous sodium hydroxide (0.1 mole) and subsequently heated to complete water removal on the water separator. The mixture was cooled to 50° C and treated with 51,4 grams (0.2 mole) of D,L-3-formyl-2,2-pentamethylene-5,5-dimethyl-thiazolidine-4-carboxylic acid. The further procedure was as in Example 1. The recovered salt of D-3-formyl-2,2-pentamethylene-5,5-dimethyl-thiazolidine-4-carboxylic acid and D-(−)-threo-1-(p-nitrophenyl)-2-amino-propanediol-1,3 was treated with 300 ml of water free warm methanol for the separation of the simultaneously formed sodium chloride. The sodium chloride was filtered off and the filtrate evaporated to dryness. There were recovered 37 grams, corresponding to 80%, of the salt of D-3-formyl-2,2-pentamethylene-5,5-dimethyl-thiazolidine-4-carboxylic acid and D-(−)-threo-1-(p-nitrophenyl)-2-amino-propanediol-1,3. It had a specific rotation of +23.5° (1 % solution in ethanol) and a melting point of 181° to 183° c.

What is claimed is:

1. A salt of an optical isomer of threo-1-(p-nitrophenyl)-2-amino-propanediol-1,3 of the formula:

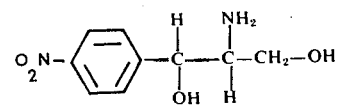

and a protected penicillamine of the formula:

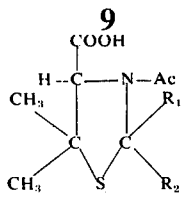

wherein Ac is benzoyl, tosyl, nitrophenylsulfenyl, formyl or acetyl and $R_1$ and $R_2$ are hydrogen, alkyl of 1 to 8 carbon atoms or $R_1$ and $R_2$ together are polymethylene of 3 to 9 carbon atoms.

2. A salt according to claim 1, wherein $R_1$ and $R_2$ are hydrogen, alkyl of 1 to 8 carbon atoms or $R_1$ and $R_2$ together are polymethylene of 4 to 5 carbon atoms.

3. A salt of claim 1 free of its antipode.

4. A salt according to claim 3 wherein Ac is formyl or acetyl.

5. A salt according to claim 2 wherein Ac is formyl or acetyl.

6. A salt according to claim 5 wherein $R_1$ and $R_2$ are both methyl.

7. A salt according to claim 6 wherein Ac is formyl.

8. A salt according to claim 7 which is the D-3-formyl-2,2,5,5-tetramethyl-thiazolidine-4-carboxylic acid and D-(−)-threo-1-(p-nitrophenyl)-2-amino propanediol-1,3.

9. A salt according to claim 7 which is the L-3-formyl-2,2,5,5-tetramethyl-thiazolidine-4-carboxylic acid and L-(+)-threo-1-(p-nitrophenyl)-2-amino-propanediol-1,3.

10. In a process for the recovery of an optically active protected penicillamine including the step of crystallizing out of solution the salt of an optically active base with either the protected D-penicillamine or protected L-penicillamine having the formula

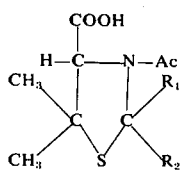

wherein Ac is benzoyl, tosyl nitrophenylsulfenyl, formyl or acetyl and $R_1$ and $R_2$ are hydrogen, alkyl of 1 to 8 carbon atoms or $R_1$ and $R_2$ together are polymethylene of 3 to 9 carbon atoms, the improvement comprising reacting the protected D,L-penicillamine of formula II with the optical isomer of (1)threo-1-p-nitrophenyl)-2-amino-propanediol-1,3 or (2) a salt thereof.

11. A process according to claim 10 wherein $R_1$ and $R_2$ are hydrogen, alkyl of 1 to 8 carbon atoms or $R_1$ and $R_2$ together are polymethylene of 4 to 5 carbon atoms.

12. The process of claim 10 wherein the optical isomer of the base is the D-(−) isomer and the salt crystallized out is the salt of protected D-penicillamine.

13. The process of claim 10 wherein the optical isomer of the base is the L-(+) isomer and the salt crystallized out is the protected salt of L-penicillamine.

14. The process of claim 10 wherein there is employed 0.1 to 3 moles of the optically active base per mole of protected D,L-penicillamine.

15. The process of claim 14 wherein there is employed 0.5 to 1.1 moles of optically active base per mole of protected D,L-penicillamine.

16. The process of claim 10 wherein $R_1$ and $R_2$ are alkyl of 1 to 8 carbon atoms and Ac is formyl or acetyl.

17. The process of claim 16 wherein $R_1$ and $R_2$ are both methyl.

18. The process of claim 17 wherein Ac is formyl.

19. The process of claim 18 wherein the optical isomer of the base is the D-(−) isomer and the salt crystallized out is the salt of D-3-formyl-2,2,5,5-tetramethyl-thiazolidine-4-carboxylic acid.

20. The process of claim 18 wherein the optical isomer of the base if the L-(+) isomer and the salt crystallized out is the salt of D-3-formyl-2,2,5,5-tetramethyl-thiazolidine-4-carboxylic acid.

21. The process of claim 10 wherein the optical isomer employed is (1).

22. The process of claim 10 wherein the optical isomer employed is the salt (2).

23. The process of claim 22 wherein the salt (2) is the hydrochloride or a carboxylic acid salt.

24. The process of claim 23 wherein the salt (2) is the hydrochloride or a 1 to 6 carbon atoms alkanoic acid salt.

* * * * *

UNITED STATES PATENT OFFICE
CERTIFICATE OF CORRECTION

Patent No. 3,980,666     Dated September 14, 1976

Inventor(s) Paul SCHERBERICH

It is certified that error appears in the above-identified patent and that said Letters Patent are hereby corrected as shown below:

Column 3, line 35 should read "acetyl-2,2,5,5-tetramethyl-thiazolidine-4-car-".

Column 7, line 27 should read "25.8 grams (0.1 mole) of D-(-)-".

Column 7, line 57, "thiazolidino" should be "thiazolidine".

Column 8, line 29, "-23°" should be "+23°".

Signed and Sealed this

First Day of March 1977

[SEAL]

Attest:

RUTH C. MASON
Attesting Officer

C. MARSHALL DANN
Commissioner of Patents and Trademarks